(12) United States Patent
Starks

(10) Patent No.: US 7,988,639 B2
(45) Date of Patent: Aug. 2, 2011

(54) SYSTEM AND METHOD FOR COMPLEX GEOMETRY MODELING OF ANATOMY USING MULTIPLE SURFACE MODELS

(75) Inventor: Daniel R. Starks, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 583 days.

(21) Appl. No.: 11/647,275

(22) Filed: Dec. 29, 2006

(65) Prior Publication Data

US 2007/0270705 A1 Nov. 22, 2007

Related U.S. Application Data

(60) Provisional application No. 60/800,858, filed on May 17, 2006.

(51) Int. Cl.
*A61B 5/04* (2006.01)
*A61B 5/02* (2006.01)
(52) U.S. Cl. .......................... 600/508; 600/424; 600/506
(58) Field of Classification Search .................. 600/424, 600/506, 508
See application file for complete search history.

(56) References Cited

U.S. PATENT DOCUMENTS

| | | | | |
|---|---|---|---|---|
| 4,548,211 A | * | 10/1985 | Marks | 600/507 |
| 4,721,114 A | | 1/1988 | DuFault et al. | |
| 4,785,399 A | | 11/1988 | Evans et al. | |
| 4,991,587 A | * | 2/1991 | Blakeley et al. | 600/483 |
| 5,217,022 A | * | 6/1993 | Nathanielsz | 600/547 |
| 5,275,164 A | | 1/1994 | Maeda et al. | |
| 5,490,516 A | * | 2/1996 | Hutson | 600/508 |
| 5,494,042 A | * | 2/1996 | Panescu et al. | 600/508 |
| 5,529,072 A | * | 6/1996 | Sramek | 600/506 |
| 5,577,509 A | * | 11/1996 | Panescu et al. | 600/508 |
| 5,662,108 A | * | 9/1997 | Budd et al. | 600/374 |
| 5,687,737 A | | 11/1997 | Branham et al. | |

(Continued)

FOREIGN PATENT DOCUMENTS

EP 609182 A1 * 8/1994

(Continued)

OTHER PUBLICATIONS

Barber, C.B., et. al., The Quickhull Algorithm for Convex Hulls, pp. 1-15 (reprint of same titled article as published in ACM Transactions on Mathematical Software, Dec. 1996, pp. 469-483, vol. 22, No. 4).

(Continued)

*Primary Examiner* — Niketa I Patel
*Assistant Examiner* — Nicole F Lavert
(74) *Attorney, Agent, or Firm* — Wiley Rein LLP

(57) ABSTRACT

Disclosed herein are methods and systems for creating a complex model of the human anatomy. The anatomy may be modeled using multiple geometries. Generally, a plurality of line-of-sight models may be combined into a composite model. Multiple clouds of points may be used to create surface models which may then be merged into a common volume. The resulting composite model may include portions that are not within a line of sight of a mean center point of the composite model. The surface models may be modeled using polygons, including for example, triangles. Disclosed herein are also ways in which electrophysiology data and/or other information may be mapped from a measurement point to a point on the composite model.

22 Claims, 7 Drawing Sheets

U.S. PATENT DOCUMENTS

| | | | | |
|---|---|---|---|---|
| 5,697,377 | A * | 12/1997 | Wittkampf | 600/374 |
| 5,889,524 | A * | 3/1999 | Sheehan et al. | 345/419 |
| 5,954,665 | A * | 9/1999 | Ben-Haim | 600/515 |
| 5,983,126 | A | 11/1999 | Wittkampf | |
| 6,075,871 | A | 6/2000 | Simanovsky et al. | |
| 6,102,869 | A * | 8/2000 | Meier et al. | 600/506 |
| 6,175,756 | B1 * | 1/2001 | Ferre et al. | 600/424 |
| 6,185,448 | B1 * | 2/2001 | Borovsky | 600/424 |
| 6,206,874 | B1 * | 3/2001 | Ubby et al. | 606/34 |
| 6,226,542 | B1 * | 5/2001 | Reisfeld | 600/407 |
| 6,236,883 | B1 * | 5/2001 | Ciaccio et al. | 600/515 |
| 6,301,496 | B1 * | 10/2001 | Reisfeld | 600/407 |
| 6,400,981 | B1 * | 6/2002 | Govari | 600/509 |
| 6,456,867 | B2 * | 9/2002 | Reisfeld | 600/407 |
| 6,575,912 | B1 * | 6/2003 | Turcott | 600/485 |
| 6,640,119 | B1 | 10/2003 | Budd et al. | |
| 6,647,617 | B1 * | 11/2003 | Beatty et al. | 29/825 |
| 6,650,927 | B1 * | 11/2003 | Keidar | 600/424 |
| 6,658,279 | B2 | 12/2003 | Swanson et al. | |
| 6,699,200 | B2 * | 3/2004 | Cao et al. | 600/508 |
| 6,704,600 | B2 * | 3/2004 | Daum | 607/30 |
| 6,728,562 | B1 | 4/2004 | Budd et al. | |
| 6,751,492 | B2 * | 6/2004 | Ben-Haim | 600/374 |
| 6,826,420 | B1 * | 11/2004 | Beatty et al. | 600/374 |
| 6,826,421 | B1 * | 11/2004 | Beatty et al. | 600/374 |
| 6,837,886 | B2 * | 1/2005 | Collins et al. | 606/41 |
| 6,839,588 | B1 * | 1/2005 | Rudy | 600/523 |
| 6,892,091 | B1 * | 5/2005 | Ben-Haim et al. | 600/509 |
| 6,922,586 | B2 * | 7/2005 | Davies | 600/547 |
| 6,939,309 | B1 * | 9/2005 | Beatty et al. | 600/508 |
| 6,947,785 | B1 | 9/2005 | Beatty et al. | |
| 6,976,967 | B2 * | 12/2005 | Dahl et al. | 600/508 |
| 6,978,168 | B2 | 12/2005 | Beatty et al. | |
| 6,983,179 | B2 * | 1/2006 | Ben-Haim | 600/374 |
| 6,990,370 | B1 * | 1/2006 | Beatty et al. | 600/509 |
| 6,996,428 | B2 * | 2/2006 | Kislov et al. | 600/393 |
| 7,076,300 | B1 | 7/2006 | Kroll et al. | |
| 7,189,208 | B1 * | 3/2007 | Beatty et al. | 600/587 |
| 2002/0007117 | A1 * | 1/2002 | Ebadollahi et al. | 600/437 |
| 2002/0062087 | A1 * | 5/2002 | Anderson et al. | 600/508 |
| 2003/0013977 | A1 * | 1/2003 | Daum | 600/508 |
| 2003/0040676 | A1 * | 2/2003 | Prentice et al. | 600/508 |
| 2003/0097061 | A1 * | 5/2003 | Ferre et al. | 600/424 |
| 2003/0160786 | A1 | 8/2003 | Johnson | |
| 2003/0236466 | A1 * | 12/2003 | Tarjan et al. | 600/508 |
| 2004/0002660 | A1 * | 1/2004 | Mielekamp | 600/508 |
| 2004/0059237 | A1 | 3/2004 | Narayan et al. | |
| 2004/0082870 | A1 | 4/2004 | Rudy et al. | |
| 2004/0254437 | A1 | 12/2004 | Hauck et al. | |
| 2005/0015003 | A1 * | 1/2005 | Lachner et al. | 600/424 |
| 2005/0182295 | A1 * | 8/2005 | Soper et al. | 600/117 |
| 2005/0203394 | A1 | 9/2005 | Hauck | |
| 2006/0015096 | A1 | 1/2006 | Hauck et al. | |
| 2006/0095022 | A1 | 5/2006 | Moll et al. | |
| 2006/0100610 | A1 | 5/2006 | Wallace et al. | |
| 2007/0057945 | A1 | 3/2007 | Olson | |
| 2007/0060833 | A1 | 3/2007 | Hauck | |
| 2007/0073179 | A1 | 3/2007 | Afonso et al. | |
| 2007/0208260 | A1 | 9/2007 | Afonso | |

FOREIGN PATENT DOCUMENTS

| | | | |
|---|---|---|---|
| EP | 1070480 | * | 1/2001 |
| GB | 2246634 A | * | 2/1992 |
| WO | 2007012989 A1 | | 2/2007 |

OTHER PUBLICATIONS

Pachon, Jose, C., et. al., "Cardioneuroablation"—new treatment for neurocardiogenic syncope, functional AV block and sinus dysfunction using catheter RF-ablation, Europace, (2005) 7, 1-13, The European Society of Cardiology.

Pachon, Jose, C., et. al., A new treatment for atrial fibrillation based on spectral analysis to guide the catheter RF-ablation, Europace, (2004) 6, 590-601, The European Society of Cardiology.

Nademanee, Koonlawee, M.D., Facc, et. al., A new approach for catheter ablation of atrial fibrillation: Mapping of the electrophysiologic substrate, Journal of the American College of Cardiology, (2004) vol. 43, No. 11, 2044-53.

Extended European Search Report for EP Application No. 07797511.8 (corresponding to PCT/US2007/069064), dated Jan. 28, 2010.

Lo, S.H., et al., "Finite element mesh generation over intersecting curved surfaces by tracing of neighbours", Finite Elements in Analysis and Design, vol. 41 No. 4, Jan. 1, 2005, pp. 351-370.

International Search Report for PCT/US07/69064 dated Jan. 30, 2008.

* cited by examiner

SYSTEM AND METHOD FOR COMPLEX GEOMETRY MODELING OF ANATOMY USING MULTIPLE SURFACE MODELS

CROSS-REFERENCE TO RELATED APPLICATIONS

This application claims the benefit of U.S. provisional application No. 60/800,858, filed 17 May 2006, entitled "System And Method For Complex Geometry Modeling Using Multiple Geometries," which is hereby expressly incorporated by reference as though fully set forth herein.

The following co-pending applications are incorporated by reference as though fully set forth herein: U.S. application Ser. Nos. 11/227,006 (filed 15 Sep. 2005 and entitled "System and Method for Three-Dimensional Mapping of Electrophysiology Information"), which is still pending, 10/819,027 (filed 6 Apr. 2004 and entitled "Method and Apparatus for Catheter Navigation and Location and Mapping in the Heart," now issued as U.S. Pat. No. 7,263,397 on 28 Aug. 2007; Ser. No. 11/647,276 (filed 29 Dec. 2006, entitled "System And Method For Mapping Electrophysiology Information Onto Complex Geometry," now issued as U.S. Pat. No. 7,774,051 on 10 Aug. 2010 (which claims benefit of U.S. provisional application No. 60/800,848, filed 17 May 2006); Ser. No. 11/647,304 filed 29 Dec. 2006; entitled "Robotic Surgical System and Method for Surface Modelling," which is still pending.

BACKGROUND OF THE INVENTION

1. Field of the Invention

The instant invention relates to imaging of complex anatomic geometries and presenting measurement information regarding specific points on the anatomy. More particularly, the present invention relates to creating a complex model of the human anatomy.

2. Background Art

The present invention relates to the creation of geometric models of the human anatomy, including for example, the human heart.

The design of an accurate anatomic modeling system carries with it the challenge of how to faithfully represent a surface of a particular anatomy bounding a cloud of data points. A number of different methodologies have been used to resolve this difficult problem. One example is referred to as "line-of-sight" modeling, which utilizes a central reference point and models a region of the anatomy based on a line-of-sight methodology. That is, all points on the model are "visible" from the central reference point (e.g., a mean center reference point).

However, if there are portions of the anatomy that are beyond the line-of-sight, then the resulting model will likely be inaccurate. This is also true for conventional modeling systems used to model the heart.

Accurate modeling is especially important when the model being generated is going to be used in connection with electrophysiology measurement points and/or for treatment.

Accordingly, a need exists for improved modeling of the interior shape of the anatomy, including for example, the interior chambers of a heart.

BRIEF SUMMARY OF THE INVENTION

The present invention overcomes the shortcomings associated with conventional line-of-sight surface modeling methods and systems by utilizing multiple geometries and then combining the geometries to provide a more accurate modeling of the heart, which improves a physician's ability to deliver effective treatment to a patient.

In accordance with one embodiment of the present invention, a method of creating a surface model of an anatomy is provided comprising the following steps: obtaining a first plurality of location points defining a first section of the anatomy, the first plurality of location points having a first mean center point from which a line of sight may be drawn to every location point of the first plurality of location points; generating a first three-dimensional surface model of the first section of the anatomy using the first plurality of location points; obtaining a second plurality of location points defining a second section of the anatomy, where the second plurality of location points have a second mean center point from which a line of sight may be drawn to every location point of the second plurality of location points. The second section of the anatomy includes at least an area of the anatomy that is not included within the first section of the anatomy, and at least one location point of the second plurality of location points is not within a line of sight of the first mean center point. The method further includes generating a second three-dimensional surface model of the second section of the anatomy using the second plurality of location points, and combining the first three-dimensional surface model with the second three-dimensional surface model to create a composite three-dimensional surface model for the first and second sections of the anatomy. The polygons used to model the first and second sections of the anatomy may be triangles defined by a plurality of edges. Optionally, the first three-dimensional surface model is disjointed from the second three-dimensional surface model.

Optionally, the process of generating a first three-dimensional surface model may include generating a first three-dimensional surface model of the first section of the anatomy using the first plurality of location points. The first three-dimensional surface model comprises a plurality of polygons, and the process of generating a second three-dimensional surface model comprises generating a second three-dimensional surface model of the second section of the anatomy using the second plurality of location points. The second three-dimensional surface model comprises a plurality of polygons.

Optionally, the combining process may include identifying a plurality of polygons of the first three-dimensional surface model lying wholly outside a volume of the second section of the anatomy; identifying a plurality of polygons of the second three-dimensional surface model lying wholly outside a volume of the first section of the anatomy; and defining a composite three-dimensional surface model comprising the plurality of identified polygons lying wholly outside the volume of the second section of the anatomy and the plurality of identified polygons lying wholly outside the volume of the first section of the anatomy. Optionally, the polygons are defined by a plurality of edges, and for each polygon of the first three-dimensional surface model that intersects with a polygon of the second three-dimensional surface model, the method includes the steps of: trimming along lines of intersection so as to discard portions of the intersecting polyhedrons that are interior to one of the first and second three-dimensional surface models, thereby creating a plurality of trimmed edges; defining new polyhedrons that use as a vertex at least one vertex of an intersecting polyhedron and using as additional vertices, points at which trimmed edges meet lines of intersection, the new polyhedrons defining an intersection surface area; and supplementing the composite three-dimensional model by adding the new polyhedrons that define the intersection surface area.

As an additional option, the method may further include the step of generating topological information for the new polyhedrons. The method may further include the steps of projecting a line from a measurement point P to one of the first mean center point and the second mean center point, and determining a point P1 on the surface of the composite three-dimensional model at which the projected line intersects the composite three-dimensional model; and associating measurement information from the measurement point P with the point P1 on the surface of the composite three-dimensional model.

As yet an additional option, the method may further, or alternatively, include the steps of: determining a point P2 on the surface of the composite three-dimensional model that is closest to a measurement point P; and associating measurement information from the measurement point P with the point P2 on the surface of the composite three-dimensional model.

The method may further, or alternatively, include the steps of: identifying a plurality of triangles of the first three-dimensional surface model lying wholly outside a volume of the second section of the anatomy; identifying a plurality of triangles of the second three-dimensional surface model lying wholly outside a volume of the first section of the anatomy; for each triangle of the first three-dimensional surface model that intersects with a triangle of the second three-dimensional surface model, trimming along lines of intersection so as to discard portions of the triangles that are interior to one of the first and second three-dimensional surface models, thereby creating a plurality of trimmed edges, and defining new triangles that define an intersection surface area, each new triangle using as a first vertex a vertex of an intersecting triangle and using as second and third vertices points at which trimmed edges of one or more intersecting triangles meet lines of intersection; and defining a composite three-dimensional surface model comprising: a) the plurality of identified triangles lying wholly outside the volume of the second section; b) the plurality of identified triangles lying wholly outside the volume of the first section; and c) the new triangles that define the intersection surface area.

Embodiments of the present invention optionally contemplate: obtaining a cardiac electrophysiology map comprising position information identifying a plurality of measurement locations and electrophysiology measurements made at each of the plurality of measurement locations; identifying location points in the composite three-dimensional surface model that are proximate the measurement locations for the identified plurality of measurement locations; and assigning at least one electrophysiology level for a measurement location to an identified location point in the composite three-dimensional surface model based on a degree of proximity between the identified location point and the measurement location.

Optionally, the methods include the following steps: inserting a measurement electrode within a portion of the heart; placing the measurement electrode at a plurality of locations along a surface of the heart; receiving position information for each of the plurality of locations along the surface of the heart; recording electrical activity at each of the plurality of locations along the surface of the heart; projecting a line from a measurement point to one of the first mean center point and the second mean center point; determining a point on the surface of the composite three-dimensional surface model at which the projected line intersects the composite three-dimensional surface model; and associating the recorded electrical activity with the point on the surface of the composite three-dimensional surface model at which the projected line intersects the composite three-dimensional surface model.

In accordance with yet another embodiment of the present invention, a method of creating a three-dimensional model of an anatomy is provided comprising the following steps: obtaining a first three-dimensional model of a first portion of an anatomy including position information for a plurality of location points within the first portion of the anatomy; obtaining a second three-dimensional model of a second portion of the anatomy including position information for a plurality of location points within the second portion of the anatomy. At least one of the first and second portions of the anatomy includes at least one area of the anatomy that is not included in the other of the first and second portions of the anatomy, and at least one of the first three-dimensional model and the second three-dimensional model is a line-of-sight geometry for which the following condition is met: every portion of the three-dimensional model is visible from a mean center point of the three dimensional model. The three-dimensional models are then combined to create a composite geometric model for the first and second portions of the anatomy having a mean center point and at least one portion not in a line of sight from the mean center point.

Optionally, in accordance with the methods of the present invention, the step of obtaining a first three-dimensional model includes: inserting an electrode within a first portion of an anatomy; placing the electrode at a plurality of location points along a surface of the first portion of the anatomy; receiving position information for each of the plurality of location points along the surface of the first portion of the anatomy; and generating a first three-dimensional model of the first portion of the anatomy comprising position information for each of the plurality of location points within the first portion of the anatomy.

Optionally, the step of obtaining a second three-dimensional model includes: receiving a data file comprising position information for each of a plurality of location points along a surface of the second portion of the anatomy, and generating a second three-dimensional model of the second portion of the anatomy comprising position information for each of the plurality of location points within the second portion of the anatomy from the data file.

Optionally, the first and second three-dimensional models may further include information formatted to identify three-dimensional spaces using a plurality of triangular facets, and wherein the step of combining the first three-dimensional model with the second three-dimensional model comprises: drawing a plurality of triangles to connect the first three-dimensional model to the second-three dimensional model; and generating data representative of a combination of the first three-dimensional model, the second three-dimensional model and the plurality of triangles drawn to connect the first three-dimensional model to the second three-dimensional model.

Alternatively, the combining step may include: identifying a plurality of triangles of the first three-dimensional model lying wholly outside a volume of the second three-dimensional model; identifying a plurality of triangles of the second three-dimensional model lying wholly outside a volume of the first three-dimensional model; for each triangle of the first three-dimensional model that intersects with a triangle of the second three-dimensional model, trimming edges of the triangle along lines of intersection so as to discard portions of the triangles that are interior to one of the first and second three-dimensional models, thereby creating a plurality of trimmed edges; defining new triangles that use as a vertex at least one vertex of an intersecting triangle and that use as additional vertices points at which trimmed edges meet lines of intersection, the new triangle defining an intersection surface area; and defining a composite geometric model for the first and second portions of the anatomy, the composite geometric model comprising: a) the plurality of identified triangles lying wholly outside the volume of the second three-dimensional model; b) the plurality of identified triangles lying wholly outside the volume of the first three-dimensional model; and c) the new triangles that define the intersection surface area. In this embodiment, the composite geometric model has a mean center point from which at least one portion of the composite geometric model is not within a line of sight.

In addition to methods, the present invention contemplates a system for presenting complex cardiac geometries to a physician comprising a modeling processor to generate a first three-dimensional model of a first portion of a heart comprising position information for a plurality of location points within the first portion of the heart and a second three-dimensional model of a second portion of the heart comprising position information for a plurality of location points within the second portion of the heart. The second portion of the heart includes an at least one area of the heart that is not included in the first portion of the heart. The system further includes a geometry processor to combine the first three-dimensional model with the second three-dimensional model to create a combined geometric model for the first and second portions of the heart. At least one point on a surface of the combined geometric model is not within a line of sight of a mean center point of the combined geometric model.

Optionally, the modeling processor further includes a display device to present the combined geometric model for the first and second portions of the heart. Additionally, the modeling processor may further include: a catheter having an electrode in a distal end of the catheter; and a localization system to determine the location of the electrode.

The first and second three-dimensional models may be comprised of a plurality of triangles. The geometry processor adds the plurality of triangles to connect the first three-dimensional model to the second-three dimensional model and generates data representative of a combination of the first three-dimensional model, the second three-dimensional model and the plurality of triangles added to connect the two three-dimensional models.

Optionally, the three-dimensional models may be comprised of a plurality of triangles defined by edges wherein at least one triangle from the first three dimensional model intersects along a line of intersection with at least one triangle from the second three dimensional model. The geometry processor then creates a combined geometric model comprising: a) a first plurality of triangles from the first three-dimensional model lying wholly outside a volume of the second three-dimensional model; b) a second plurality of triangles from the second three-dimensional model lying wholly outside a volume of the first three-dimensional model; c) at least one transition triangle having three vertices: a first vertex that is common to a triangle of one of the first and second three-dimensional models that intersects with a triangle from the other of the first and second three dimensional models; a second vertex that is defined by a point at which an edge of a triangle from the first three dimensional model intersects with the second three dimensional model; and a third vertex that is defined by a point at which an edge of a triangle from the second three dimensional model intersects with the first three dimensional model. The combined geometric model has a mean center point from which at least one portion of the combined geometric model is not within a line of sight.

The foregoing and other aspects, features, details, utilities, and advantages of the present invention will be apparent from reading the following description and claims, and from reviewing the accompanying drawings.

DETAILED DESCRIPTION OF THE INVENTION

The present invention improves a system's ability to create an accurate model of an anatomy, especially an interior surface of an anatomy. The present invention provides systems and methods for presenting complex cardiac geometries to a physician, preferably including a modeling processor to generate a first three-dimensional model of a first portion of a heart comprising position information for a plurality of location points within the first portion of the heart and a second three-dimensional model of a second portion of the heart comprising position information for a plurality of location points within the second portion of the heart. The second portion of the heart includes at least one area of the heart that is not included in the first portion of the heart. The methods and systems preferably further include a geometry processor to combine the first three-dimensional model with the second three-dimensional model to create a combined geometric model for the first and second portions of the heart. The combined geometric model may include at least one point on its surface that is not within a line of sight of a mean center point of the combined geometric model.

The present invention is not limited to creating accurate models of the heart, but for illustrative purposes, reference will often be made herein to a navigation and localization system used for assessment and treatment of cardiac tissue.

The methodology described herein would be equally applicable to modeling other parts of the human anatomy. For purposes of illustrating the present invention, the techniques for modeling a chamber of a patient's heart will now be described.

Figure 1:
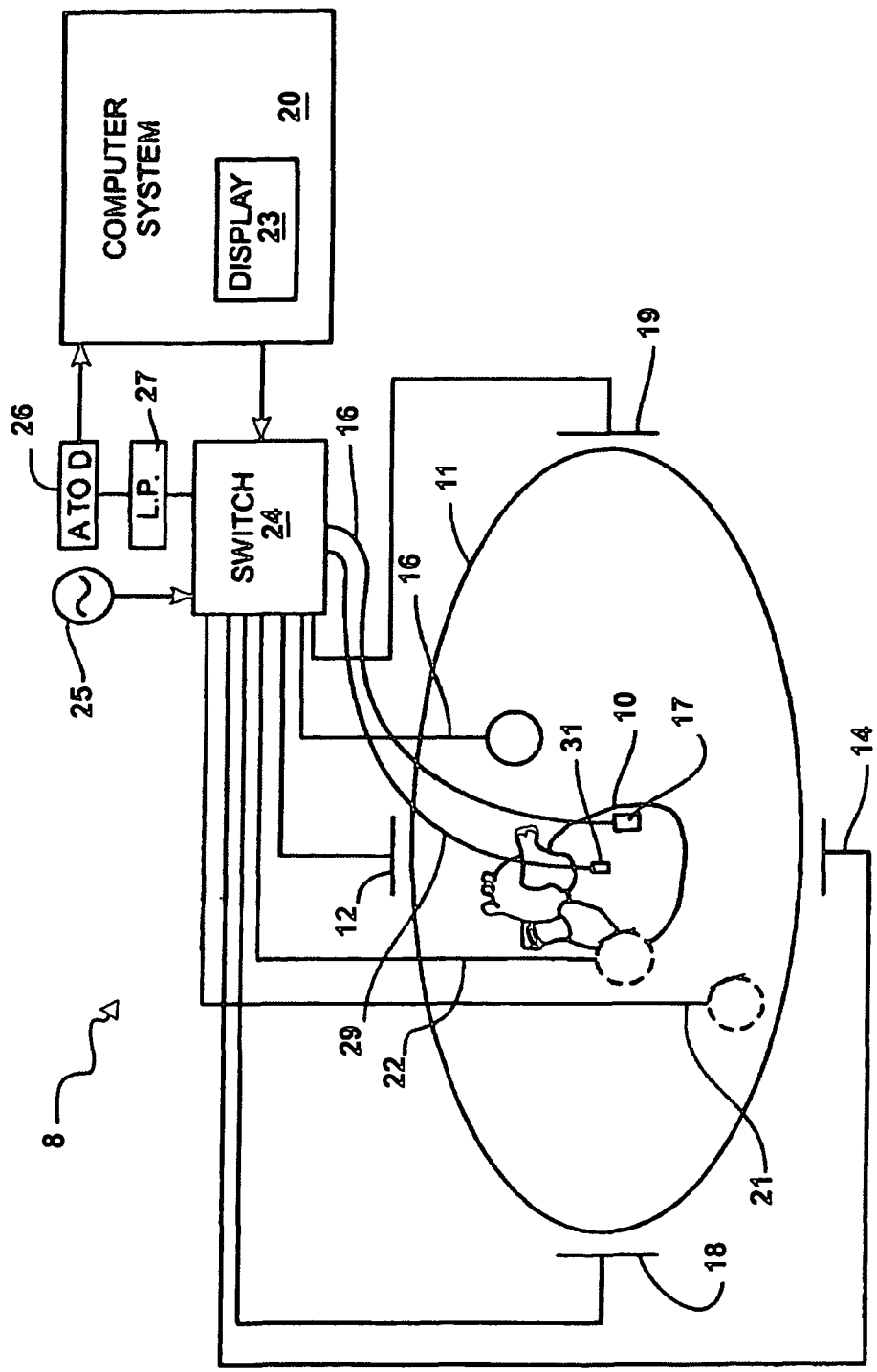
FIG. 1 is a schematic diagram of a system for performing a cardiac electrophysiology examination or ablation procedure wherein the location of one or more electrodes can be determined and recorded.

FIG. 1 shows a schematic diagram of a localization system 8, preferably including a modeling processor and a geometry processor as part of the computer system 20, according to the present invention for conducting cardiac electrophysiology studies by navigating a cardiac catheter and measuring electrical activity occurring in a heart 10 of a patient 11 and three-dimensionally mapping the electrical activity and/or information related to or representative of the electrical activity. System 8 can be used to help create an anatomical model using one or more electrodes. System 8 can also be used to measure electrophysiology data at a plurality of points along a cardiac surface, and store the measured data in association with location information for each measurement point at which the electrophysiology data was measured.

The patient 11 is depicted schematically as an oval for simplicity. Three sets of surface electrodes (e.g., patch electrodes) are shown applied to a surface of the patient 11 along an X-axis, a Y-axis, and a Z-axis. The X-axis surface electrodes 12, 14 are applied to the patient along a first axis, such as on the lateral sides of the thorax region of the patient (e.g., applied to the patient's skin underneath each arm) and may be referred to as the Left and Right electrodes. The Y-axis electrodes 18, 19 are applied to the patient along a second axis generally orthogonal to the X-axis, such as along the inner thigh and neck regions of the patient, and may be referred to as the Left Leg and Neck electrodes. The Z-axis electrodes 16, 22 are applied along a third axis generally orthogonal to the X-axis and the Y-axis, such as along the sternum and spine of the patient in the thorax region and may be referred to as the Chest and Back electrodes. The heart 10 lies between these pairs of surface electrodes. An additional surface reference electrode (e.g., a "belly patch") 21 provides a reference and/or ground electrode for the system 8. The belly patch electrode 21 is an alternative to a fixed intra-cardiac electrode 31. It should also be appreciated that in addition, the patient 11 will have most or all of the conventional electrocardiogram (ECG) system leads in place. This ECG information is available to the system 8 although not illustrated in FIG. 1.

A representative catheter 13 having at least one electrode 17 (e.g., a distal electrode) is also shown. This representative catheter electrode 17 is referred to as the "roving electrode" or "measurement electrode" throughout the specification. Typically, multiple electrodes on catheter 13, or on multiple such catheters, will be used. In one embodiment, for example, the system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

An optional fixed reference electrode 31 (e.g., attached to a wall of the heart 10) is also shown on a second catheter 29. For calibration purposes, this electrode 31 may be stationary (e.g., attached to or near the wall of the heart) or disposed in a fixed spatial relationship with the roving electrode 17. The fixed reference electrode 31 may be used in addition or alternatively to the surface reference electrode 21 described above. In many instances, a coronary sinus electrode or other fixed electrode in the heart 10 can be used as a reference for measuring voltages and displacements.

Each surface electrode is coupled to the multiplex switch 24 and the pairs of electrodes are selected by software running on a computer 20, which couples the electrodes to a signal generator 25. The computer 20, for example, may comprise a conventional general-purpose computer, a special-purpose computer, a distributed computer, or any other type of computer. The computer 20 may comprise one or more processors, such as a single central-processing unit, or a plurality of processing units, commonly referred to as a parallel processing environment. Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across an intra-cardiac electrode 17 resulting from a predetermined set of drive (source-sink) configurations are combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, e.g., the belly patch 21, while the unexcited electrodes measure voltage with respect to the ground reference. The measurement electrode 17 placed in the heart 10 is exposed to the field from a current pulse and is measured with respect to ground, e.g., the belly patch 21. In practice the catheters within the heart may contain multiple electrodes and each electrode potential may be measured. As previously noted, at least one electrode may be fixed to the interior surface of the heart to form a fixed reference electrode 31, which is also measured with respect to ground. Data sets from each of the surface electrodes, the internal electrodes, and the virtual electrodes are all used to determine the location of the measurement electrode 17 or other electrodes within the heart 10. One of skill in the art will readily appreciate that the measurement electrode 17 can also be used to measure electrophysiology data and system 8 can be used to store the electrophysiology data in associated with location information for the measurement point at which the electrophysiology data was measured.

The modeling processor and geometry processor may be comprised of any combinations of hardware and software options known to those of skill in the art. For example, in a preferred embodiment, the modeling processor includes a localization/mapping system, such as the ENSITE NAVX™ navigation and visualization system of St. Jude Medical, Atrial Fibrillation Division, Inc. Other localization systems, however, may be used in connection with the present invention, including for example, the CARTO™ navigational and location system of Biosense Webster, Inc. The localization and mapping systems described in the following patents (all of which are incorporated by reference in the entireties) can be used with the present invention: U.S. Pat. Nos. 6,990,370; 6,978,168; 6,947,785; 6,939,309; 6,728,562; 6,640,119; 5,983,126; and 5,697,377. The geometry processor, is similarly comprised of any combination of hardware and software options known to those of ordinary skill in the art. For example, in a preferred embodiment, the geometry processor is a software solution designed to interact with the information generated from the modeling processor to provide the combined geometric model.

Figure 2:
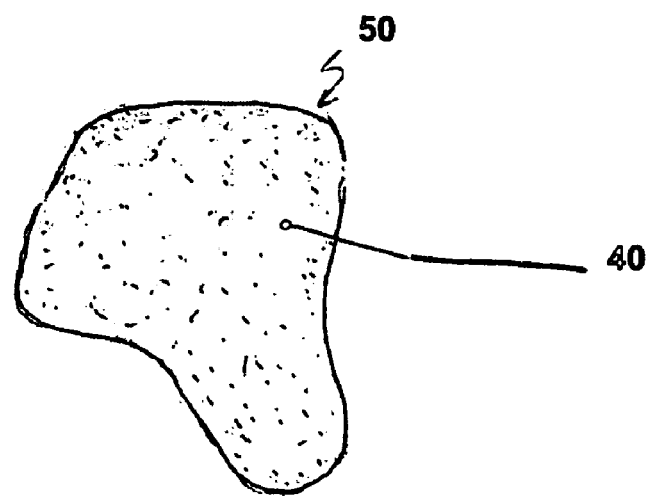
FIG. 2 is a schematic representation of cloud of location data points.

To create a cloud of data points, one or more intracardiac electrodes 17 may be moved randomly, pseudo-randomly, or according to one or more preset patterns within a chamber of a patient's heart while system 8 measures the location of the one or more electrodes 17 to create a cloud 50 of data points 40 by providing location data identifying position data for each data point 40 of the cloud 50. FIG. 2 illustrates an example of a cloud 50 of points 40 that could be created using such a technique. Generally, the outermost data points 40 within cloud 50 will correspond to the interior wall of the heart chamber in a relaxed or diastole state corresponding to its greatest volume.

Figure 3:
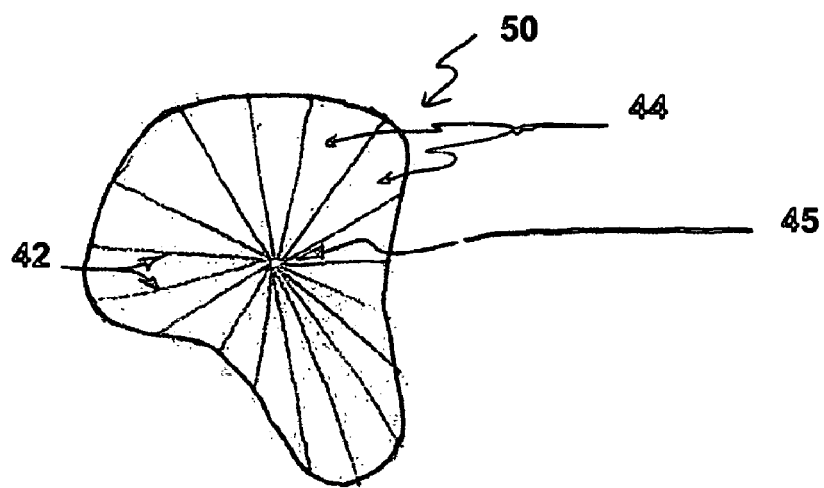
FIG. 3 is a schematic diagram of an exemplary methodology for binning the cloud of points.
Figure 4:
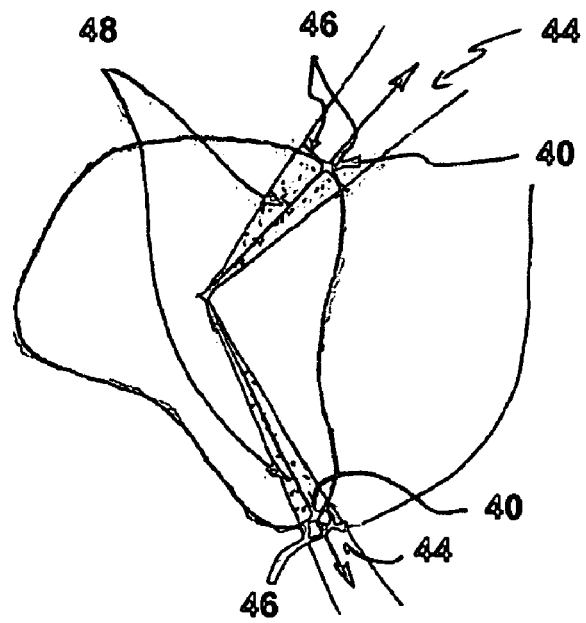
FIG. 4 is a schematic diagram of an exemplary methodology for constructing a surface of an anatomy utilizing a line-of-sight methodology.

One technique of fitting a surface to the cloud 50 of points 40 assumes that the entire surface is "visible" from a reference point, for example as shown in FIG. 3. Such a surface is described as being in the "line of sight" when viewed from the reference point. That is, a straight line 42 may be drawn from the reference point to any point on the surface without passing outside of the boundary defined by cloud 50 of points 40. One common way of choosing a reference point for a line-of-sight surface fitting is to determine a mean center point 45 for the cloud 50 of points 40. The mean center point 45 may be determined using known algorithms, including, without limitation, those used for determining a centroid of cloud 50 of points 40. The surface model is then created by growing radial slices outward from the mean center point 45, as shown in FIGS. 3-4 As illustrated in FIG. 3, a shell or surface may be rendered from this location data by fitting an array of radial "bins" 44 around groups 48 of the position data points 40. As illustrated in FIG. 4, the bins 44 are constructed based on the mean center point 45 within the cloud 50 of data points 40 and then extending borders radially outward from the center point 45. The bins 44 extend to the furthest data point 40 within the slice encompassed by the bin 44. It should be noted that even though FIG. 3 is schematically presented in two dimensions, the bins 44 are three-dimensional volumes. The radial end faces 46 of the bins 44 thus approximate the surface of the heart chamber wall. Common geometric smoothing algorithms can then be employed to "smooth" the surface of the shell thus created out of the radial end faces 46 of the bins 44.

Ultimately, the surface of the volume is defined as a discretized representation. Preferably, the discretized representation comprises polygons, and more preferably, the discretized representation comprises triangular planar "facets" that share common corners (vertices) and maintain "topology" information about their adjacency to other facets. Techniques for modeling surfaces using triangular facets are known, including, for example the Delaunay triangulation methodology.

Figure 5:
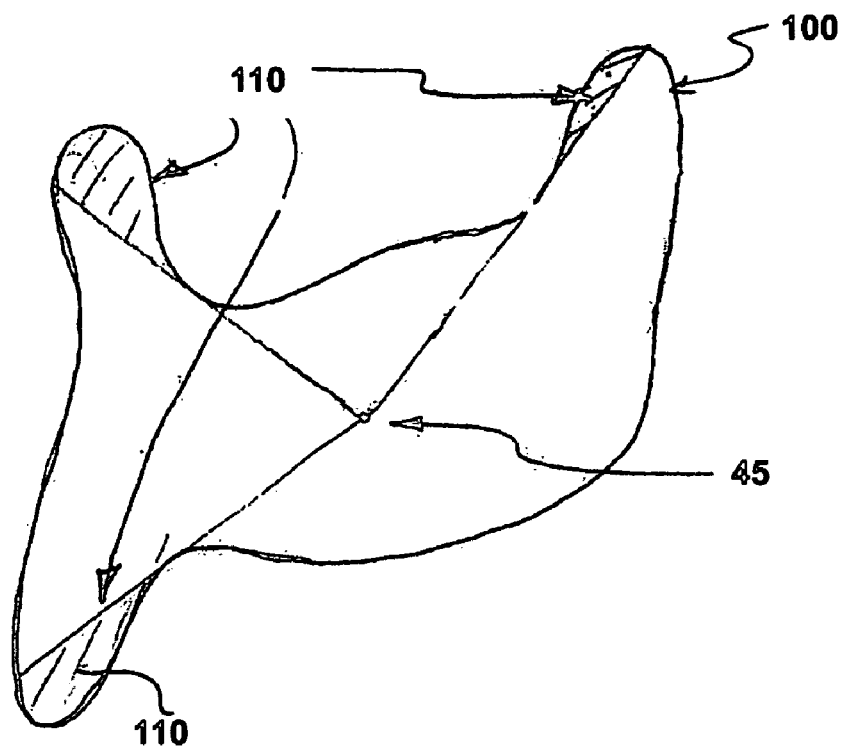
FIG. 5 is a schematic representation of an exemplary complex surface with portions that are not in a line of sight of the mean center point.
Figure 6:
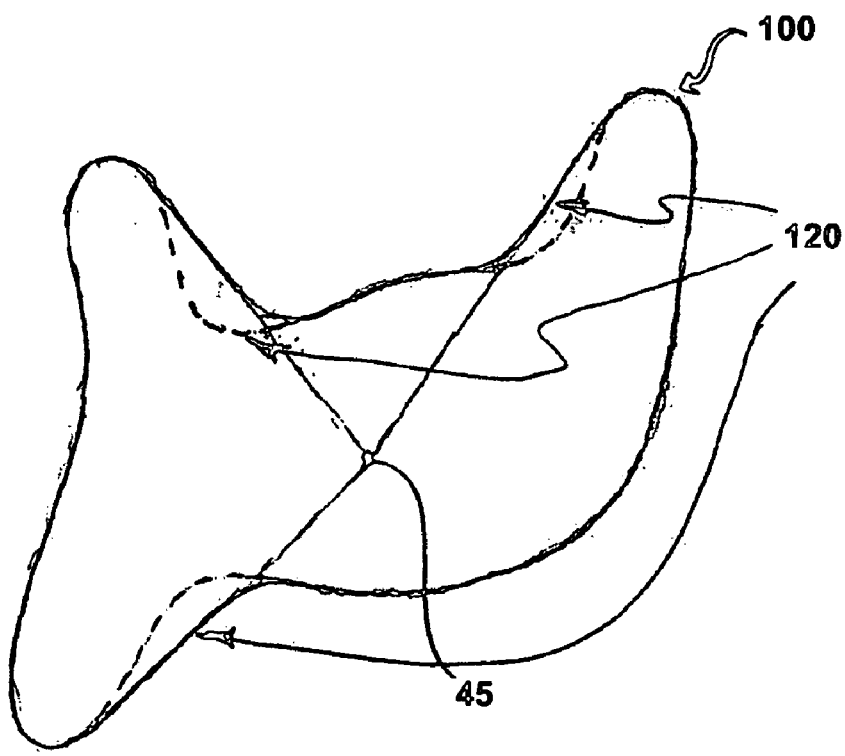
FIG. 6 is a schematic representation of an exemplary problem associated with modeling complex surfaces such as the one in FIG. 5.

As discussed above, this surface creation method assumes that the entire surface is within the line of sight of the mean center point 45. This assumption is not always met, however, when modeling anatomical structures of the human body. Accordingly, this technique does not generate an accurate representation of shapes such as shown, for example, in FIG. 5. The entire surface of complex surface 100 is not "visible" from the mean center point 45. Indeed, complex surface 100 has three hidden areas 110 that are not "visible" from mean center point 45. One of ordinary skill will recognize that, with a surface such as complex surface 100, there will be hidden areas regardless of where the reference point is placed for modeling the surface. If one attempts to compensate for the hidden areas, the result will be inaccurate modeling as illustrated in FIG. 6, where false volumes 120 are included due to the lack of flexibility in the line-of-sight model.

The present invention provides a solution to deriving a more accurate representation of the true surface shape by using the above described surface modeling technique multiple times, each time using a portion of the point cloud that lies in a different region of the anatomical structure being modeled. For example, complex surface 100 can be segmented into at least three separate geometries, each of which may be accurately modeled using the described line-of-sight methodology discussed above. The individual geometries may then be combined, and the result is an accurate surface model that overcomes the line of sight restrictions.

Figure 7:
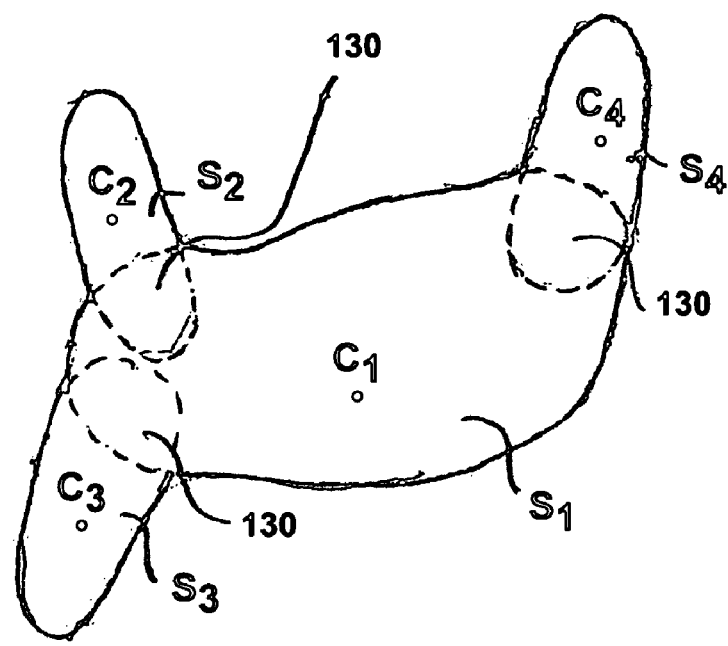
FIG. 7 is a schematic representation illustrating how an exemplary complex surface may be segmented into multiple line-of-sight geometries.
Figure 8:
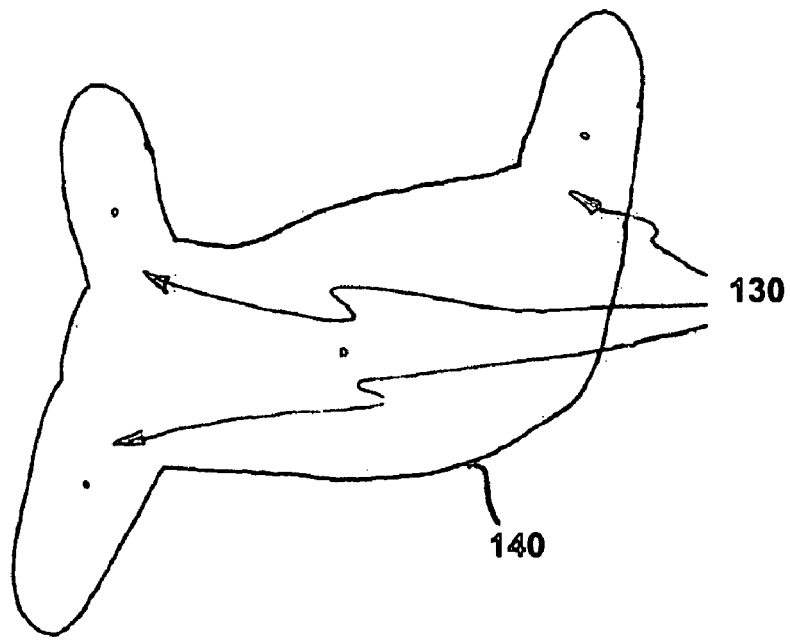
FIG. 8 is a schematic representation of an exemplary complex surface after the multiple line-of-sight geometries of FIG. 7 are merged using a Boolean function.

This segmentation technique is illustrated in FIG. 7, which segments complex surface 100 into 4 line-of-sight surfaces, namely surfaces S1, S2, S3 and S4 (which have respective mean center points C1, C2, C3 and C4). As exemplified in FIG. 8, the volumes of the individual surfaces are merged, or combined, into a composite volume, the interior portions 130 of the surfaces are effectively removed from the geometries, such that the remaining data points define complex surface 140.

One way to accomplish combining the individually-created surfaces into one composite is by performing a Boolean OR operation on the volumes enclosed by the surfaces and keeping the portions of original surface that bound this volume. For example, geometrical Boolean operators are available in various software libraries, including without limitation the IRIT LIBRARY™ available through Technion. When more than two surfaces are involved, the Boolean operations are performed pair-wise, with the result of each operation being used as one of the inputs for the next Boolean operation.

A challenge with combining multiple volumes is determining the points that define the intersection of the two volumes. FIGS. 9-12 illustrate one way in which the present invention solves this challenge. In particular, the plurality of line-of-sight surfaces S1, S2, S3, and S4 are merged into a composite surface 140.

In the case where the surface of each volume is defined as a discretized representation comprising triangular planar "facets" that share common corners (vertices) and topology information concerning adjacent facets, the combining procedure begins by identifying those facets from each surface that lie wholly outside the volume enclosed by the other surface and keeping the identified facets in the resulting composite surface. It also identifies those facets that intersect one or more facets from the other surface. These facets are trimmed along the line(s) of intersection—that is the line(s) that are formed where the triangular facets intersect each other. The resulting facet fragments that lie outside the volume enclosed by the other surface are triangulated and kept in the resulting combined surface. As a final step, the topological information for new facets resulting from trimming is generated, as shown in FIG. 11.

Figure 9:
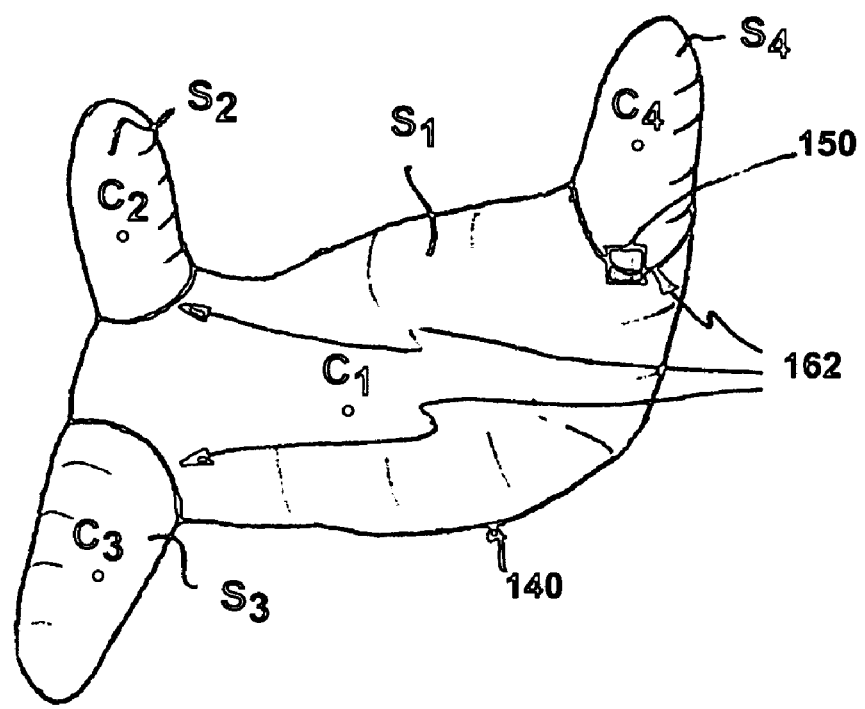
FIG. 9 is a schematic representation of an exemplary complex surface highlighting the intersections between the multiple line-of-sight geometries of FIG. 7.
Figure 10:
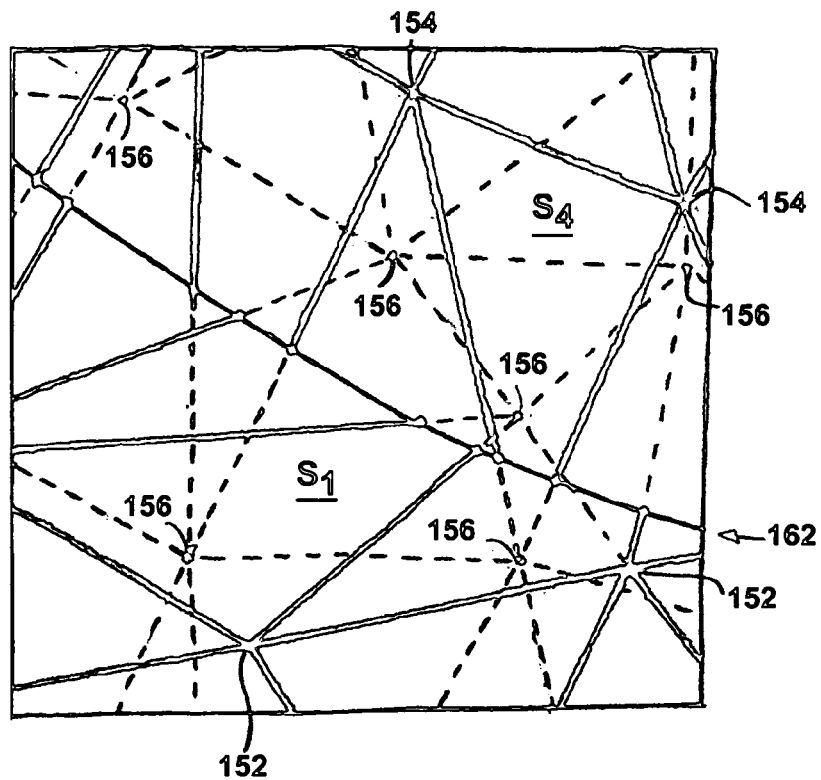
FIG. 10 is a exploded view of the line of intersection identified in FIG. 9.

FIG. 10 shows an exploded discretized representation taken from 150 of FIG. 9 of two surfaces S1 and S4 prior to being combined. FIG. 10 illustrates how triangulated facets from two different representations may intersect and further, how to define new data points to define the intersection. Surface S1 (which has mean center point C1) is defined by triangulated facets that are drawn with green lines, and surface S4 (associated with line-of-sight mean center point C4) is defined by triangulated facets that are drawn with red lines. The intersections of solid green lines define the original vertices 152 for surface S1, while the intersections of solid red lines define the original vertices 154 for surface S4. In FIG. 10, the dashed lines represent that portion of the triangular facet that is deemed to be interior of, or overlapping, the other volume. In other words, the triangular facets and portions of triangular facets that are defined by solid lines (red and green) define the exterior, or non-overlapping, discretized surface.

Figure 11:
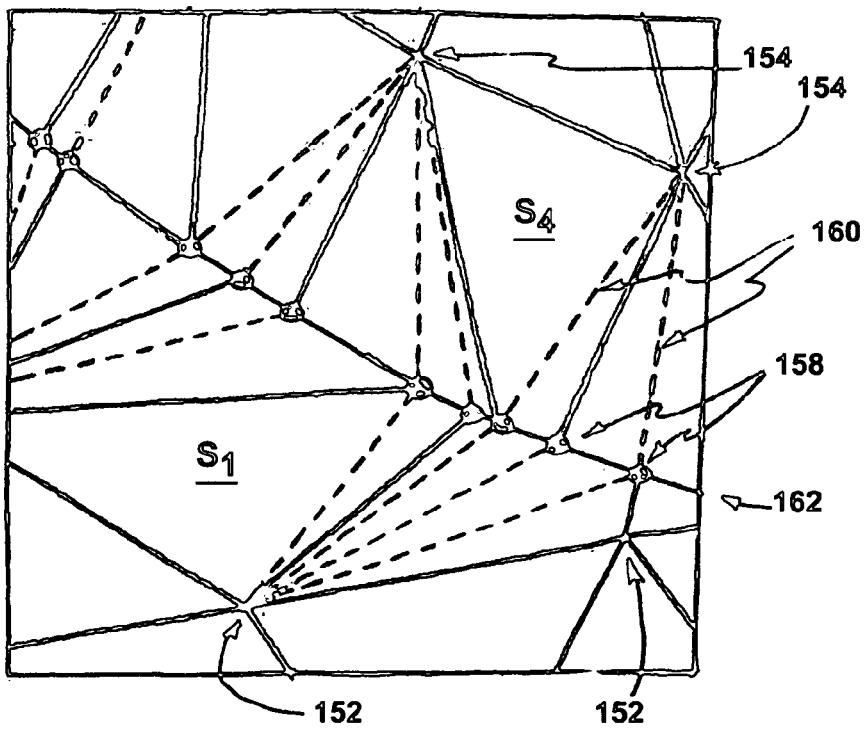
FIG. 11 is a exploded view detailing how new polygons are created to help define the surface along the lines of intersection between the multiple geometries identified in FIG. 9.

In FIG. 11, the portions of the original facets 156 that are interior of the composite volume have been removed based on the assumption that the interior polygons have been trimmed away. The point at which a solid line (red or green) intersects the trim line is deemed to define a new vertex such that a new triangular facet 158 is created. The dotted lines (red or green) shown in FIG. 11 have a different significance than the dotted lines shown in FIG. 10. In FIG. 11, the dotted lines represent newly defined edges 160 that comprise triangular facets that help define the intersection 162 of the surface S1 with surface S4.

Computer processes can be programmed to implement the merger steps, as well as the creation of a composite model. A computer process is preferred for trimming portions of the polyhedrons along the lines of intersection, and similarly, for defining the vertices for the triangular facets that will define the surface along the lines of intersection.

A challenge with defining new data points for the intersection 162 is recognized when electrophysiology data, originally associated with points 40 within cloud 50, is mapped to the composite surface. Maintaining a correct surface topology is important for subsequent operations performed on the composite surface, such as finding shortest paths and distances between points on the surface, creating free-form cutouts of the surface, properly interpolating map data on the surface, and creating iso-contours for data maps. It is acknowledged that measurements taken at data points near the intersection of merged surfaces will likely not match the newly defined vertices that define the newly defined triangular facets defining the surface near the intersection. Thus, the original measurement points must be projected onto an appropriate surface or surface point, and in practical use, items such as labels or anatomical markers must be projected onto the composite surface.

Figure 12:
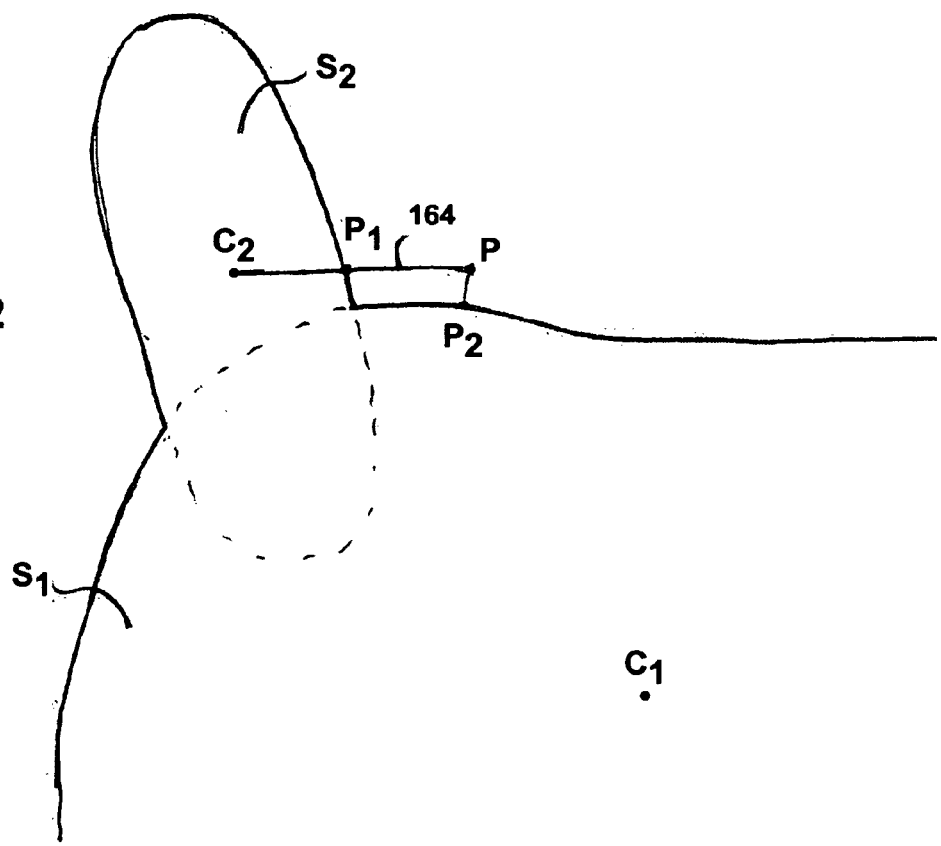
FIG. 12 illustrates how information regarding a measurement point may be projected onto a composite geometry.

The present invention presents at least two ways in which the projection of measurement points, labels and/or anatomical markers may be projected onto the composite surface. In the first method, if it is known onto which of the original (unmerged) surfaces an item should project, then the item can be projected toward the center point of that surface until it intersects the surface. This is illustrated in FIG. 12. For example, if it is known that point P lies on the original surface S2 (which has a mean center point C2), then a line 164 is projected from P toward C2, and wherever this projected line intersects the surface of S2 is the point P1 at which the information associated with point P is projected. This technique illustrates the importance of saving topology information associated with the data points that define a surface before they are merged with another surface.

The second technique is yet another way to effect a projection. It can be used in conjunction with, or in place of, the first technique. Here, point P is simply projected to the closest point on the composite surface. This is illustrated in FIG. 12 as well. Here, point P is projected simply to the closest surface point P2. Since P2 is closer than P1, the projection according to the second technique yields a different result from the application of the first technique. One of ordinary skill will appreciate that multiple ways exist to identify the closest data point to a particular reference point.

While the present invention is described above in the context of triangular planar facets, this is for illustrative purposes only, and does not limit the present invention. The methodology described herein would be equally applicable to other polygons that could be used to model the surfaces at issue.

Furthermore, while the present invention was illustrated in the context of overlapping surface areas, the present invention applies equally to non-overlapping surface areas. By way of example, and with reference to FIG. 7, the present invention would apply to an effort to combine surface S3 with surface S4 (which are not overlapping).

Although multiple embodiments of this invention have been described above with a certain degree of particularity, those skilled in the art could make numerous alterations to the disclosed embodiments without departing from the spirit or scope of this invention. For example, while the description above describes data being mapped to a three-dimensional model, data may be mapped to any map including, but not limited to, a two- or three-dimensional, static or time-varying image or model. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of creating a surface model of an anatomy, comprising:

obtaining a first plurality of location points defining a first section of the anatomy, said first plurality of location points having a first mean center point from which a line of sight may be drawn to every location point of the first plurality of location points;

generating a first three-dimensional surface model of the first section of the anatomy using the first plurality of location points;

obtaining a second plurality of location points defining a second section of the anatomy, said second plurality of location points having a second mean center point from which a line of sight may be drawn to every location point of the second plurality of location points, wherein said second section of the anatomy includes at least an area of the anatomy that is not included within the first section of the anatomy, and wherein at least one location point of the second plurality of location points is not within a line of sight of the first mean center point;

generating a second three-dimensional surface model of the second section of the anatomy using the second plurality of location points; and combining the first three-dimensional surface model with the second three-dimensional surface model to create a composite three-dimensional surface model for the first and second sections of the anatomy.

2. The method of claim 1, wherein the process of generating a first three-dimensional surface model comprises:

generating a first three-dimensional surface model of the first section of the anatomy using the first plurality of location points, wherein said first three-dimensional surface model comprises a plurality of polygons; and wherein the process of generating a second three-dimensional surface model comprises generating a second three-dimensional surface model of the second section of the anatomy using the second plurality of location points, wherein said second three-dimensional surface model comprises a plurality of polygons.

3. The method of claim 2, wherein the combining process comprises:

identifying a plurality of polygons of the first three-dimensional surface model lying wholly outside a volume of the second section of the anatomy;

identifying a plurality of polygons of the second three-dimensional surface model lying wholly outside a volume of the first section of the anatomy; and defining a composite three-dimensional surface model comprising the plurality of identified polygons lying wholly outside the volume of the second section of the anatomy and the plurality of identified polygons lying wholly outside the volume of the first section of the anatomy.

4. The method of claim 3, wherein the polygons are defined by a plurality of edges, the method further comprising:
for each polygon of the first three-dimensional surface model that intersects with a polygon of the second three-dimensional surface model, trimming along lines of intersection so as to discard portions of one or more intersecting polyhedrons that are interior to one of the first and second three-dimensional surface models, thereby creating a plurality of trimmed edges;
defining new polyhedrons that use as a vertex at least one vertex of an intersecting polyhedron of the one or more intersecting polyhedrons and using as additional vertices points at which trimmed edges meet lines of intersection, the new polyhedrons defining an intersection surface area; and
supplementing the composite three-dimensional model by adding the new polyhedrons that define the intersection surface area.

5. The method of claim 4, further comprising generating topological information for the new polyhedrons.

6. The method of claim 4, further comprising:
projecting a line from a measurement point P to one of the first mean center point and the second mean center point, and determining a point P1 on the surface of the composite three-dimensional model at which the projected line intersects the composite three-dimensional model; and
associating measurement information from the measurement point P with the point P1 on the surface of the composite three-dimensional model.

7. The method of claim 4, further comprising:
determining a point P2 on the surface of the composite three-dimensional model that is closest to a measurement point P; and
associating measurement information from the measurement point P with the point P2 on the surface of the composite three-dimensional model.

8. The method of claim 2, wherein the polygons used to model the first and second sections of the anatomy are triangles, and wherein the triangles are defined by a plurality of edges.

9. The method of claim 8, where in the combining process comprises:
identifying a plurality of triangles of the first three-dimensional surface model lying wholly outside a volume of the second section of the anatomy;
identifying a plurality of triangles of the second three-dimensional surface model lying wholly outside a volume of the first section of the anatomy;
for each triangle of the first three-dimensional surface model that intersects with a triangle of the second three-dimensional surface model, trimming along lines of intersection so as to discard portions of the triangles that are interior to one of the first and second three-dimensional surface models, thereby creating a plurality of trimmed edges; and
defining new triangles that define an intersection surface area, each new triangle using as a first vertex a vertex of an intersecting triangle and using as second and third vertices points at which trimmed edges of one or more intersecting triangles meet lines of intersection; and
defining a composite three-dimensional surface model comprising: a) the plurality of identified triangles lying wholly outside the volume of the second section; b) the plurality of identified triangles lying wholly outside the volume of the first section; and c) the new triangles that define the intersection surface area.

10. The method of claim 1, wherein the first three-dimensional surface model is disjointed from the second three-dimensional surface model.

11. The method of claim 1, further comprising:
obtaining a cardiac electrophysiology map comprising position information identifying a plurality of measurement locations and electrophysiology measurements made at each of the plurality of measurement locations;
identifying location points in the composite three-dimensional surface model that are proximate the measurement locations for the identified plurality of measurement locations; and
assigning at least one electrophysiology level for a measurement location to an identified location point in the composite three-dimensional surface model based on a degree of proximity between the identified location point and the measurement location.

12. The method of claim 1, further comprising:
inserting a measurement electrode within a portion of the heart;
placing the measurement electrode at a plurality of locations along a surface of the heart;
receiving position information for each of the plurality of locations along the surface of the heart;
recording electrical activity at each of the plurality of locations along the surface of the heart;
projecting a line from a measurement point to one of the first mean center point and the second mean center point;
determining a point on the surface of the composite three-dimensional surface model at which the projected line intersects the composite three-dimensional surface model; and
associating the recorded electrical activity with the point on the surface of the composite three-dimensional surface model at which the projected line intersects the composite three-dimensional surface model.

13. A system for presenting complex cardiac geometries to a physician comprising:
a modeling processor to generate a first three-dimensional model of a first portion of a heart comprising position information for a plurality of location points within the first portion of the heart and a second three-dimensional model of a second portion of the heart comprising position information for a plurality of location points within the second portion of the heart,
wherein the second portion of the heart includes at least one area of the heart that is not included in the first portion of the heart; and
a geometry processor to combine the first three-dimensional model with the second three-dimensional model to create a combined geometric model for the first and second portions of the heart, wherein at least one point on a surface of said combined geometric model is not within a line of sight of a mean center point of the combined geometric model.

14. The system of claim 13, wherein the modeling processor further comprises a display device to present the combined geometric model for the first and second portions of the heart.

15. The system of claim 13, wherein the modeling processor further comprises:
a catheter having an electrode in a distal end of the catheter; and
a localization system to determine the location of the electrode.

16. The system of claim 13, wherein each of the first and second three dimensional models comprises a plurality of triangles; wherein the geometry processor adds a plurality of triangles to connect the first three-dimensional model to the second-three dimensional model; and wherein the geometry processor generates data representative of a combination of the first three-dimensional model, the second three-dimensional model and the plurality of triangles added to connect the first three-dimensional model to the second three-dimensional model.

17. The system of claim 13, wherein each of the first and second three dimensional models comprises a plurality of triangles defined by edges, and wherein at least one triangle from the plurality of triangles comprising the first three dimensional model intersects along a line of intersection with at least one triangle from the plurality of triangles comprising the second three dimensional model, and wherein the geometry processor creates a combined geometric model comprising:
  a) a first plurality of triangles from the first three-dimensional model lying wholly outside a volume of the second three-dimensional model;
  b) a second plurality of triangles from the second three-dimensional model lying wholly outside a volume of the first three-dimensional model;
  c) at least one transition triangle having three vertices: a first vertex that is common to a triangle of one of the first and second three-dimensional models that intersects with a triangle from the other of the first and second three dimensional models; a second vertex that is defined by a point at which an edge of a triangle from the first three dimensional model intersects with the second three dimensional model; and a third vertex that is defined by a point at which an edge of a triangle from the second three dimensional model intersects with the first three dimensional model;
  wherein said combined geometric model has a mean center point from which at least one portion of the combined geometric model is not within a line of sight.

18. A method of creating a three-dimensional model of an anatomy, comprising:
  obtaining a first three-dimensional model of a first portion of an anatomy, said first three-dimensional model comprising position information for a plurality of location points within the first portion of the anatomy;
  obtaining a second three-dimensional model of a second portion of the anatomy, said second three-dimensional model comprising position information for a plurality of location points within the second portion of the anatomy,
  wherein at least one of the first and second portions of the anatomy includes at least one area of the anatomy that is not included in the other of the first and second portions of the anatomy;
  wherein at least one of the first three-dimensional model and the second three-dimensional model is a line-of-sight geometry for which the following condition is met: every portion of the three-dimensional model is visible from a mean center point of the three dimensional model; and
  combining the first three-dimensional model with the second three-dimensional model to create a composite geometric model for the first and second portions of the anatomy, said composite geometric model having a mean center point and at least one portion not in a line of sight from the mean center point.

19. The method of claim 18, wherein the step of obtaining a first three-dimensional model comprises:
  inserting an electrode within a first portion of an anatomy;
  placing the electrode at a plurality of location points along a surface of the first portion of the anatomy;
  receiving position information for each of the plurality of location points along the surface of the first portion of the anatomy; and
  generating a first three-dimensional model of the first portion of the anatomy comprising position information for each of the plurality of location points within the first portion of the anatomy.

20. The method of claim 19, wherein the step of obtaining a second three-dimensional model comprises:
  receiving a data file comprising position information for each of a plurality of location points along a surface of the second portion of the anatomy; and
  generating a second three-dimensional model of the second portion of the anatomy comprising position information for each of the plurality of location points within the second portion of the anatomy from the data file.

21. The method of claim 20, wherein the first and second three-dimensional models further comprise information formatted to identify three-dimensional spaces using a plurality of triangular facets, and wherein the step of combining the first three-dimensional model with the second three-dimensional model comprises:
  drawing a plurality of triangles to connect the first three-dimensional model to the second-three dimensional model; and
  generating data representative of a combination of the first three-dimensional model, the second three-dimensional model and the plurality of triangles drawn to connect the first three-dimensional model to the second three-dimensional model.

22. The method of claim 20, wherein the first and second three-dimensional models further comprise information formatted to identify three-dimensional spaces using a plurality of triangles, and wherein the step of combining the first three-dimensional model with the second three-dimensional model comprises:
  identifying a plurality of triangles of the first three-dimensional model lying wholly outside a volume of the second three-dimensional model;
  identifying a plurality of triangles of the second three-dimensional model lying wholly outside a volume of the first three-dimensional model;
  for each triangle of the first three-dimensional model that intersects with a triangle of the second three-dimensional model, trimming edges of the triangle along lines of intersection so as to discard portions of the triangles that are interior to one of the first and second three-dimensional models, thereby creating a plurality of trimmed edges;
  defining new triangles that use as a vertex at least one vertex of an intersecting triangle and that use as additional vertices points at which trimmed edges meet lines of intersection, the new triangle defining an intersection surface area; and
  defining a composite geometric model for the first and second portions of the anatomy, said composite geometric model comprising: a) the plurality of identified triangles lying wholly outside the volume of the second three-dimensional model; b) the plurality of identified triangles lying wholly outside the volume of the first three-dimensional model; and c) the new triangles that define the intersection surface area;
  wherein said composite geometric model has a mean center point from which at least one portion of the composite geometric model is not within a line of sight.

* * * * *